(12) United States Patent
McCoard et al.

(10) Patent No.: US 9,375,413 B2
(45) Date of Patent: Jun. 28, 2016

(54) METHODS OF REDUCING MILK SOMATIC CELL COUNT

(71) Applicant: AgResearch Limited, Hamilton (NZ)

(72) Inventors: Sue McCoard, Hamilton (NZ); Quentin Sciascia, Hamilton (NZ); Danitsja van der Linden, Hamilton (NZ)

(73) Assignee: AGRESEARCH LIMITED, Hamilton (NZ)

( * ) Notice: Subject to any disclaimer, the term of this patent is extended or adjusted under 35 U.S.C. 154(b) by 0 days.

(21) Appl. No.: 14/701,443

(22) Filed: Apr. 30, 2015

(65) Prior Publication Data

US 2015/0313860 A1 Nov. 5, 2015

(30) Foreign Application Priority Data

May 2, 2014 (NZ) ........................................ 624360

(51) Int. Cl.
*A61K 31/198* (2006.01)
*A23C 9/14* (2006.01)

(52) U.S. Cl.
CPC ................. *A61K 31/198* (2013.01); *A23C 9/14* (2013.01)

(58) Field of Classification Search
None
See application file for complete search history.

(56) References Cited

U.S. PATENT DOCUMENTS 5,585,098 A * 12/1996 Coleman .............. A61K 39/085
424/150.1

OTHER PUBLICATIONS

Al-Dabbas et al, "The effect of arginine supplementation on some blood parameters, ovulation rate and concentrations of estrogen and progesterone in female Awassi sheep," Pakistan Journal of Biological Sciences (2008) 11(20): 2389-2394.
Chacher et al., "Effect of dietary N-carbamoylglutamate on milk production and nitrogen utilization in high-yielding dairy cows," J. Dairy Sci. (2014) 97:2338-2345.
Chacher et al., "Potential role of N-carbamoyl glutamate in biosynthesis of arginine and its significance in production of ruminant animals," Journal of Animal Science and Biotechnology (2013) 4:16, 6 pages.
Fligger et al, "Arginine Supplementation Increases Weight Gain, Depresses Antibody Production, and Alters Circulating Leukocyte Profiles in Preruminant Calves Without Affecting Plasma Growth Hormone Concentrations," Journal of Animal Science (1997) 75(11): 3019-3025.

* cited by examiner

*Primary Examiner* — Yevegeny Valenrod
(74) *Attorney, Agent, or Firm* — Morrison & Foerster LLP (57) ABSTRACT

Provided are methods of reducing milk somatic cell count using L-arginine supplementation of lactating ruminant animals during gestation, and/or during the lactation phase post parturition to decrease somatic cell count in milk produced by the animals.

15 Claims, 5 Drawing Sheets

METHODS OF REDUCING MILK SOMATIC CELL COUNT

CROSS REFERENCE TO RELATED APPLICATIONS

This application claims priority to and the benefit of New Zealand Patent Application No. NZ624360, filed on May 2, 2014, the entire contents of which is incorporated herein by reference in its entirety.

TECHNICAL FIELD

Described herein are methods of reducing milk somatic cell count. More specifically, methods are described using L-arginine supplementation of lactating ruminant animals during gestation, and/or during the lactation phase post parturition to decrease somatic cell count in milk produced by the animals.

BACKGROUND ART

Milk somatic cell (MSC) count is a measure used widely in the dairy industry for milk quality. Somatic cell count is a measure of the white blood cell concentration in milk—not necessarily all white blood cells are captured by this measure but a majority are, primarily leukocytes.

The importance of MSC count in milk processing relates primarily to the issue of mastitis infection. Mastitis is an infection caused by pathogenic bacteria. One major bacteria species that causes a rise in MSC count is *Staphylococcus aureus*.

When a lactating animal is infected, the somatic cell count increases in milk from the animal. An elevated MSC count is a serious issue in milk production. Milk with a high MSC count may needed to be partitioned from a full batch and blended with low MSC count milk to make it allowable for consumption. In worst cases, the milk produced may have to be discarded. Since most automated milking operations milk many animals at once, high MSC count milk from one animal may mix with other animals' milk cause an entire milking run to be contaminated. A further drawback of mastitis infection, even at relatively low levels of infection is that the volume of milk produced by the animal decreases, thereby reducing profitability. Other issues with elevated MSC count in milk include reduced shelf life and adversely altered sensory attributes.

As should be appreciated, avoiding infection and methods to lower MSC count are important to avoid rejection of milk for consumption and to generally ensure the health of an animal.

Arginine is an amino acid. In animals, arginine is classified as a semi-essential or conditionally essential amino acid. In healthy humans, arginine is seldom needed as a supplement since the body usually produces significant amounts. Despite this, many supplements exist with arginine (the L form predominantly) for human use with purported effects of increasing blood flow supporting muscle growth and supporting muscle recovery.

In non-human animals, research into the effects of L-arginine supplementation is less complete and much of the research completed to date is for mono-gastric animals. As may be appreciated, ruminants such as bovine and ovine species provide a different challenge to mono-gastric animals and active compounds useful for mono-gastric animals do not necessarily show the same efficacy in ruminant animals.

One art document, Al Dabbas 2008[1] describes administration of arginine to sheep via different routes of administration and measured the subsequent changes in plasma white blood cell counts and changes in white blood cell composition. Al Dabbas showed an increase in white blood cell levels and variations in white blood cell composition, but importantly, Al Dabbas did not use animals during gestation, a time period when many metabolic pathways change or vary from the norm. Al Dabbas also did not measure the effects of a long-term dose, instead only trialling the effects of a one off dose, hence the longevity of the effects were unknown from Al Dabbas. Further, Al Dabbas only measured plasma and not milk, and did not consider somatic cell count.

[1] Al-Dabbas, F. M., A. H. Hamra, et al. (2008). "The effect of arginine supplementation on some blood parameters, ovulation rate and concentrations of estrogen and progesterone in female Awassi sheep." Pakistan Journal of Biological Sciences 11(20): 2389-2394.

Another paper, Fligger 1997[2] found results that led away from that of Al Dabbas. In Fligger, non-gestational (and pre-ruminant) calves were administered L-arginine. The resulting antibody production was measured in the animal plasma. The results of Fligger showed a reduction in antibody production, a finding that goes against the results of Al Dabbas. This different result illustrates the incompleteness of research in relation to arginine for animals.

[2] Fligger, J. M., C. A. Gibson, et al. (1997). "Arginine Supplementation Increases Weight Gain, Depresses Antibody Production, and Alters Circulating Leukocyte Profiles in Preruminant Calves Without Affecting Plasma Growth Hormone Concentrations." Journal of Animal Science 75(11): 3019-3025.

As noted above, L-arginine is known as a supplement and has been shown to have an impact on the immune system. The art rarely investigates the effects on ruminants (animals known to have quite different metabolisms to monogastric animals). In addition the prior art is focused on animals outside of gestation and further, the art looks at plasma changes and not changes in milk or MSC count. Treatment of gestational ruminants and the impact on milk from the animal, particularly post parturition, is to the inventor's knowledge not studied in the art nor are the effects obvious given the different physiological factors.

As may be appreciated, it may be advantageous to reduce milk somatic cell count in ruminants or at least to provide the public with a choice.

Further aspects and advantages of the process and product will become apparent from the ensuing description that is given by way of example only.

SUMMARY

Described herein are methods of elevating blood plasma arginine levels of lactating ruminants to decrease somatic cell count in milk produced.

In a first aspect there is provided a method of decreasing somatic cell count in the milk from a lactating ruminant comprising administering a compound effective to elevate blood plasma arginine levels in the ruminant, said compound administered during the gestation time period and/or during the lactation phase post parturition.

In a second aspect there is provided a method of improving mammary gland health in a ruminant as measured via somatic cell count in milk produced comprising administering a compound effective to elevate blood plasma arginine levels, said compound administered during the gestation time period and/ or during the lactation phase post parturition.

In a third aspect there is provided use of a therapeutically effective amount of L-arginine, NCG or NAG, or a functional analogue of L-arginine, NCG or NAG, in the manufacture of a medicament administered during the gestation time period of a lactating ruminant and/or during the lactation phase post parturition, thereby decreasing the somatic cell count in the milk from the lactating ruminant.

In a fourth aspect there is provided use of a therapeutically effective amount of L-arginine, NCG or NAG, or a functional analogue of L-arginine, NCG or NAG, in the manufacture of a medicament administered during the gestation time period and/or during the lactation phase post parturition, thereby improving mammary gland health in the ruminant as measured via somatic cell count in milk produced.

Advantages of the above methods and uses include the ability to directly influence MSC count during gestation and/or during the lactation phase. The findings show that L-arginine administration has a direct and positive impact on mammary health and milk produced by the ruminant. The result is avoidance of issues associated with mastitis infection, improved quality milk and better animal efficiency through avoidance of infection. A lower dependence on antibiotics is a further advantage. A further surprising result was how administration could be stopped at parturition yet the effects on the milk lasted well beyond parturition showing that administration with L-arginine had a residual effect. A yet further advantage was that administration with L-arginine did not reduce milk volume and in fact may even increase volume.

BRIEF DESCRIPTION OF THE DRAWINGS

Further aspects of the methods and uses will become apparent from the following description that is given by way of example only and with reference to the accompanying drawings in which.

DETAILED DESCRIPTION

As noted above, described herein are methods of elevating blood plasma arginine levels of lactating ruminants to decrease somatic cell count in milk produced.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term "ruminant" and grammatical variations thereof is used herein in a broad sense and includes pseudoruminants such as ungulate animals with three-chambered stomachs. The term "pseudoruminant" includes camelids such as llamas, alpacas and camels.

The term 'therapeutically effective amount' or grammatical variations thereof, with reference to an amount or dosage of a composition described herein, refers to an amount of a composition that is sufficient to cause a therapeutic effect. The term "therapeutic" as used herein is used in a broad sense and includes eliciting positive or desirable effects in the body of an animal other than solely treatment of disease.

The term 'lactation performance' refers to the milk produced from a lactating ruminant animal having substantially the same volume of production and substantially similar quality measures as a non-L-arginine administered animal with an MSC count of 500,000/ml or less.

The compounds administered according to the invention are defined as being administered during the gestation time period and/or during the lactation phase post parturition. As used herein this phasing includes administration for only part of the gestation time period and/or part of the lactation phase post parturition, as well as administration for the entire duration of either or both periods.

In a first aspect there is provided a method of decreasing somatic cell count in the milk from a lactating ruminant comprising administering a compound effective to elevate blood plasma arginine levels in the ruminant, said compound administered during the gestation time period and/or during the lactation phase post parturition In a second aspect there is provided a method of improving mammary gland health in a ruminant as measured via somatic cell count in milk produced comprising administering a compound effective to elevate blood plasma arginine levels, said compound administered during the gestation time period and/or during the lactation phase post parturition.

The animal as described above is a ruminant. The animal may be a bovine, caprine, cervine or ovine species. The animal may be a dairy cow. The animal may be a sheep. As should be appreciated, the method may also be useful for other ruminants such as goats, deer and llamas and others however key commercial embodiments are likely to lie with cows, goats and sheep given the importance of these animals to the human food chain.

As noted above, the somatic cell count in milk produced by the ruminant animal is lowered by the step of administering L-arginine. The time period during which the MSC count may be lowered may be both during administration and after administration. The longevity of the reduction post administration was unexpected and is described in more detail below. In one embodiment, the inventor's have found that the somatic cell count may be at least 10, or 15, or 20, or 25, or 30, or 35, or 40, or 45, or 50% lower than that of a comparable animal not supplemented with L-arginine. Expressed in terms of actual somatic cell count, the somatic cell count in milk from the treated animal may be less than approximately 600,000, or 500,000, or 400,000, or 300,000, or 200,000, or 100,000 cells/ml. The milk somatic cell count from the treated animals may also be further characterised by comprising greater than approximately 90, or 91, or 92, or 93, or 94, or 95, or 96, or 97, or 98, or 99% inactive macrophages (MΦ). In the udder of healthy sheep, the milk somatic cell (MSC) count is low (<500,000/ml), and the population is almost exclusively made up of inactive macrophages, with the remaining cell population consisting of polymorphonuclear leukocytes (2-28%) and lymphocytes (11-20%). At the onset of an intramammary infection (IMI), MSCs provide the first line of defence. If this first line of defence is breached, cytokine signalling is utilised to activate the production of nitric oxide (NO) in mammary epithelial cells, increasing gland vascularity and allow the recruitment of other immune cells, mainly neutrophils, into the milk to fight the infection, leading to an increased MSC count. At this stage of infection the MSC count can range from medium (500,000-1,000,000/ml) to high (1,000,000-2,000,000/ml), with a population consisting of activated neutrophils, MΦ and other immune effector cells. L-arginine administration as described above appears to maintain an MSC count well below even a medium level of infection.

Whilst the exact mechanism for the methods shown are not known, the inventor's envisage this may be because plasma MΦs and neutrophils were able to utilise the extra L-arginine to increase intracellular concentrations of amino acids (AA's) required to produce cytotoxic reactive oxygen species (ROS).

By way of background, all MSC counts are derived from the circulating plasma, where, in response to a diverse range of biological signals, they migrate to the mammary gland. Milk MΦ are commensal residents of the mammary, where they play a role in removing cellular debris, modulating gland development and protecting the uninfected mammary gland from IMI pathogens. When IMI pathogens invade the gland, milk MΦs phagocytise the pathogens and destroy them with proteases and NO. If the milk MΦs cannot effectively defend the gland they use chemoattractants to recruit other immune cells from the plasma. Neutrophils are the predominant immune cell type mobilised to fight both acute/clinical and chronic/subclinical IMI. Ruminant neutrophils are unable to produce NO like MΦs, instead they produce other cytotoxic reactive oxygen species (ROS) such as hydrogen peroxide ($H_2O_2$), hypochlorous acid (HOCL) and tyrosyl radicals to kill invading pathogens. The production of ROS by MΦs and neutrophils requires L-arginine and L-ornithine as substrates. L-arginine is metabolized in MΦs by inducible nitric oxide synthase to produce the potent cytotoxic ROS, NO and by arginase I and arginase II to synthesize L-ornithine and urea. The production of $H_2O_2$ by neutrophils is catalysed by super oxide dismutase (SOD), whilst the production of HOCL and tyrosyl radicals are catalysed by myeloperoxidase (MPO) from $H_2O_2$. L-arginine, L-ornithine and L-citrulline provide the direct precursors necessary for the production $H_2O_2$, HOCL and tyrosyl radicals by neutrophils. Exogenous L-ornithine and L-arginine supplementation to whole human blood stimulates unactivated neutrophil production of $H_2O_2$, increases MPO activity, and elevates intracellular concentrations of arginine and citrulline, whilst only arginine supplementation elevates intracellular ornithine, an important precursor as noted above.

From their investigations, it is understood by the inventor's that ruminant animals administered L-arginine were able to resist infection and keep MSC count low during and after administration because plasma MΦs and neutrophils were able to utilise the extra L-arginine and L-ornithine to increase intracellular concentrations of AAs required to produce cytotoxic ROS. When MΦs and neutrophils migrated to the gland increased intracellular concentrations of ROS substrate AAs "primed" the MΦs and neutrophils, making them more cytotoxic than those from control animals. The observation that L-arginine administered ruminant animals had significantly lower MSC count than control animals between day 1 and day 4 post parturition and administration stopping suggests that "primed" MΦs may be sufficient to eliminate the IMI before the recruitment of neutrophils is necessary. Alternatively, "primed" neutrophils may be recruited during the day 1 to day 4 time period and are able to rapidly respond to the IMI and be cleared from the gland before SCC measurement at day 4.

Research by the inventors, which is the subject of a co-pending application, has demonstrated that N-carbamoyl glutamate (NCG) and N-acetyl glutamate (NAG) can also elicit similar elevations in plasma arginine levels in ruminants to those elicited by administration of L-arginine. Accordingly, the present invention extends to the use of NCG or NAG or functional analogues thereof in the methods of the invention.

In one embodiment, the ruminant animal may receive a dose of L-arginine equivalent to at least approximately 100, or 200, or 300, or 400, or 500, or 600, or 700, or 800, or 900, or 1000, or 1500, or 2000, or 2500, or 3000, or 3500, or 4000, or 4500, or 5000 µmol/kg body weight per day. In one embodiment, the dose may be approximately 300, or 310, or 320, or 330, or 340, or 350, or 360, or 370, or 380, or 390, or 400 µmol/kg body weight administered three times a day. In other embodiments, the ruminant may receive a dose NCG or NAG, or a functional analogue of L-arginine, NCG or NAG, equivalent to elicit the same changes in plasma arginine levels as the aforementioned L-arginine doses. As may be appreciated, the dose used may vary based on a number of factors such as by animal species, animal metabolism, purity of L-arginine used, route of administration used, and whether the L-arginine has been formulated and what if any impact that has on metabolism of the L-arginine. Administration may also not be daily and may instead be twice or more daily or instead only one dose every two or more days. The above figures are provided by way of illustration only and variations may occur to address various factors including those noted above.

The L-arginine, NCG or NAG, or a functional analogue of L-arginine, NCG or NAG, may be administered orally or parenterally. The route of administration may be varied although it is anticipated that for ease of administration oral methods may be useful. For example, animal drinking water may include the L-arginine. However, as demonstrated by the inventor's, parenteral injection methods are effective and may be useful in certain environments.

Where parenteral administration is used, the L-arginine, NCG or NAG, or a functional analogue of L-arginine, NCG or NAG, may be administered via intravenous and/or intramammary injection. The preferred injection site may vary depending on the animal and the formulation of the compound used.

Where oral administration is used, the L-arginine, NCG or NAG, or a functional analogue of L-arginine, NCG or NAG, may be formulated prior to administration into a rumen-protected form. L-arginine may be destroyed in the rumen and hence not be metabolised further or at least be sufficiently destroyed as to not confer the desired somatic cell reduction. Rumen protected forms of L-arginine may be useful to have the L-arginine pass through the rumen in a known and controllable quality hence allowing a known level of this compound to be metabolised. Rumen protective formulations are known and could be adapted to suit L-arginine and the methods and uses described herein.

As noted above, administration may be completed during gestation. A critical development phase of the ruminant mammary gland is during pregnancy. The size of the mammary gland precipitously increases to support an elevation in the number, size and milk production potential of secretory cells. At parturition, the number of secretory cells in the mammary gland are close to their maximum complement, while secretory cell milk production potential remains plastic. Because of these changes and the importance of the mammary gland at this stage, intervention strategies may be useful to maximise animal health and health of progeny from the animal.

The time period during gestation that L-arginine, NCG or NAG, or a functional analogue of L-arginine, NCG or NAG, may be administered may commence from mid to late gestation. In one embodiment administration may commence from approximately day 50, or 55, or 60, or 65, or 70, or 75, or 80 or 85, or 90, or 95, or 100, or 105, or 110, or 115, or 120 of gestation. Administration may end at parturition. The inventor's found that administration did not need to be for the full gestation time period and starting administration into the gestation time period was sufficient to cause the noted decrease in somatic cell count and increased animal health.

As noted above, administration of L-arginine may end at parturition. The inventor's found that administration may be stopped at parturition and the beneficial effects may linger well after administration stopped. In one embodiment, somatic cell count remains reduced in milk produced by the lactating ruminant animal for at least approximately 5 or 10, or 11, or 12, or 13, or 14, or 15, or 16, or 17, or 18, or 19, or 20, or 21 days post parturition.

Administration may instead continue or be initiated post parturition into the lactation phase. Administration may continue for at least 1, or 2, or 3, or 4, or 5, or 6, or 7, or 8, or 9, or 10, or 11, or 12, or 13, or 14 day(s) or more post parturition. A similar lingering effect is anticipated on somatic cell count where administration is continued post parturition.

One useful result of the above methods of administration may be that the methods do not alter the lactation performance of the animal. The inventor's found that the milk production volume and milk quality may remain unchanged or even improved relative to non-administered animals in the time period post parturition.

In a third aspect there is provided use of a therapeutically effective amount of L-arginine, NCG or NAG, or a functional analogue of L-arginine, NCG or NAG in the manufacture of a medicament administered during the gestation time period of a lactating ruminant and/or during the lactation phase post parturition, thereby decreasing the somatic cell count in the milk from the lactating ruminant.

In a fourth aspect there is provided use of a therapeutically effective amount of L-arginine, NCG or NAG, or a functional analogue of L-arginine, NCG or NAG in the manufacture of a medicament administered during at least part of the gestation time period, and/or during the lactation phase post parturition, thereby improving mammary gland health in the ruminant animal as measured via somatic cell count in milk produced from the lactating ruminant.

Advantages of the above methods and uses include the ability to directly influence MSC count during gestation and/or post parturition. The findings show that L-arginine administration works during gestation and administration has a direct and positive impact on mammary health and milk produced by the ruminant. The result is avoidance of issues associated with mastitis infection, improved quality milk and better animal efficiency through avoidance of infection. A further surprising result was how administration could be stopped at parturition yet the effects on the milk lasted well beyond parturition showing that administration with L-arginine had a residual effect. A yet further advantage was that administration with L-arginine did not reduce milk volume and in fact may even increase volume.

The embodiments described above may also be said broadly to consist in the parts, elements and features referred to or indicated in the specification of the application, individually or collectively, and any or all combinations of any two or more said parts, elements or features, and where specific integers are mentioned herein which have known equivalents in the art to which the embodiments relates, such known equivalents are deemed to be incorporated herein as of individually set forth, Where specific integers are mentioned herein which have known equivalents in the art to which this invention relates, such known equivalents are deemed to be incorporated herein as if individually set forth.

WORKING EXAMPLES

The above described methods and uses are now described by reference to a study completed by the inventor's.

Example 1

A study was conducted to determine the effects of L-arginine supplementation to sheep.

Methodology—Animals and Treatments

Twin-bearing, multiparous Romney ewes were housed in individual stalls and fed once daily, a lucerne-based pellet diet formulated to meet 100% of the NRC-recommended maintenance requirements for twin-bearing pregnant and lactating ewes throughout the trial.

From day 100 of pregnancy to parturition, ewes received either an injected bolus of L-arginine-mono-hydrochloride (L-arginine-HCL; Merck KGaA, Darmstadt, Germany; 345 μmol/kg body weight (BW)) or a control being approximately the same volume of sterile saline injected three times daily (0800, 1600, 2400 hrs).

At the first sign of labour induction, which was between 1 and 10 hours (h) prior to birth, L-arginine treatment ceased and ewes were allowed to lamb naturally. In total 25 ewes were used (arginine group, n=13; control group n=12).

Methodology—Milking and Sample Analysis

Ewes were assigned to milking groups based on parturition date. Collection of a colostrum sample within the 12 h post partum could have compromised animal behaviour and ewe-lamb bond formation. Therefore, a range of 0.58-1.22 days in lactation was produced when the "colostrum" sample was collected. Ewes were then milked approximately at day 1, 4, 7, 10 and 14 of lactation, using the oxytocin method. At each milking, ewes were milked by machine followed by hand stripping, after an intravenous injection of 1 IU of synthetic oxytocin (Oxytocin V, 10 IU/mL). The time when the udder was empty was recorded. Animals were milked again (machine and hand-stripping) approximately 4 h later, with the time and weight of the milk recorded. Lambs were separated from the ewes and bottle-fed as required during the intervening period, using the milk collected from their respective dam. The same operators milked all ewes on each occasion in this study using a mobile milking machine. Milk obtained after the 4 h intervening period was subsampled for analysis of milk composition (% fat, % crude protein (CP), % lactose and somatic cell count). Milk samples were preserved with bronopol and refrigerated at 4° C. until analysis using a FT120-FTIR, calibrated for sheep milk. Two reference checks (fat and CP) were taken during lactation to account for changes in the matrix of the milk due to stage of lactation. Somatic cell counts were determined using a bromide based fluorescent dye and a FOSS flow Cytometer and values log transformed. Ewes were weighed and body condition scored (scale of 1 to 5) once a week.

Throughout milking, dams and offspring were housed in individual pens immediately adjacent to each other. Daily milk yield was calculated. Repeated measures analysis of milk yield and composition using the MIXED procedure with a linear model that included the fixed effects of dam, dam treatment group, and the covariates average dam live weight, average dam body condition score and days in lactation were included in the model. From the 25 ewes available only 18 were used for statistical analysis (arginine group n=8; control group n=10). One ewe had an infected udder and was removed from the trial after day 1, while six ewes had blind udders which significantly impacted milk yield.

Methodology—Milk Free Amino Acid Profiles

Milk free amino acids (FAA) were analysed using High-Performance Liquid Chromatography (HPLC). Skim milk (500 µL) was mixed with 500-4, lithium extraction buffer (14 g/L lithium chloride, 3 g/L lithium hydroxide, 1 g/L phenol, 50 g/L sulfosalic acid) and placed on ice for 15 to 20 min. Volumes of 10-µL lithium hydroxide (5.88 M) were added to the sample to obtain a final pH of 1.5 to 2. This was followed by centrifugation at 13,680×g for 5 min at 4° C., and the resulting supernatant was filtered through a 4 mm 0.2 µm syringe filter. The filtered sample was analysed for FAA using a Shimadzu LC 10Ai HPLC, fitted with a high-efficiency lithium-ion exchange column (3 mm i.d.×150 mm) Injected volumes were 10 µL, the reagent flow rate was 0.3 mL/min, and the run was 162 min between injections, using lithium buffers as elutants and ninhydrin post column derivatization. Free amino acid values are reported as µmol per liter of milk. Differences between treatment groups were analysed using the MIXED procedure (SAS) with a linear model that included the fixed effects of dam, dam treatment group, and the covariates average dam live weight, average dam body condition score and days in lactation were included in the model.

Figure 1A:
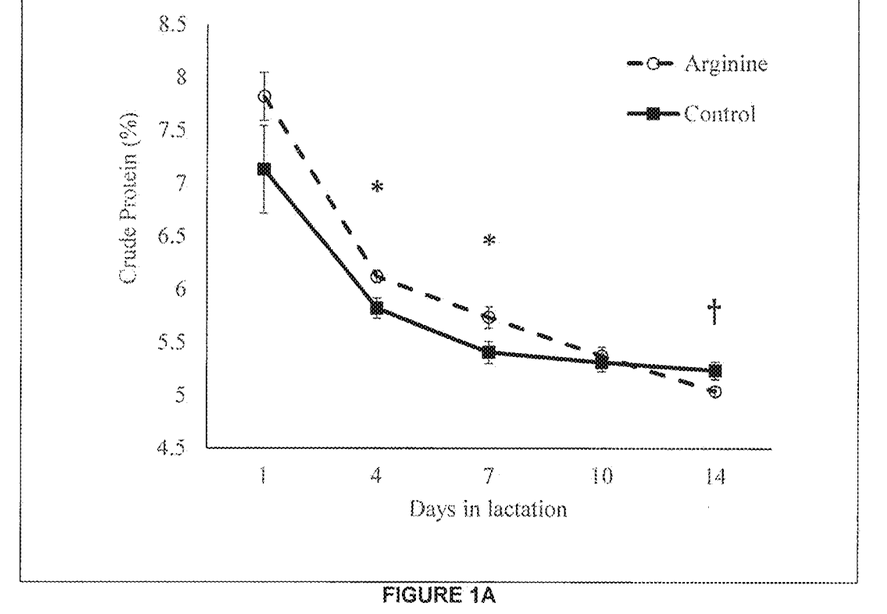
FIG. 1A is a graph from a study completed by the inventors illustrating differences in crude protein percentage in L-arginine treated ewes compared to saline-treated control ewes post parturition and L-arginine administration.

Results—Milk Composition (Crude Protein, Somatic Cell Count, Fat and Lactose) and Milk Yield Crude protein percentage was increased from day 4-7 in L-arginine treated ewes, compared to saline-treated controls (FIG. 1A).

A trend for increased crude milk protein percentage was observed in saline-treated controls at day 14 compared to L-arginine-treated ewes (FIG. 1A).

Figure 1B:
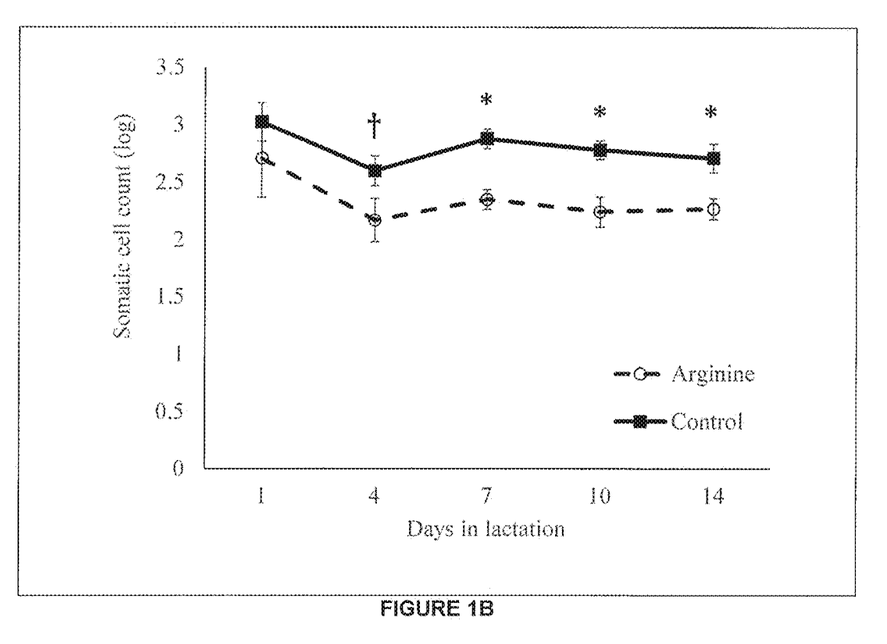
FIG. 1B is a graph from the above study illustrating differences in somatic cell count in L-arginine treated ewes compared to saline-treated control ewes post parturition and L-arginine administration.

Milk somatic cell counts were decreased from day 4-14 in L-arginine treated ewes, compared to saline-treated controls (FIG. 1B). In this study, the MSC count for untreated ewes was higher than 500,000, whereas ewes treated with L-arginine had MSC counts below 300,000. Multiple non-infectious factors can also increase MSC counts in sheep, with the most significant being parity, stage of lactation, season, flock, flock management and diurnal variation. Non-infectious factors were discounted from contributing to the observed increase in MSC count because all animals were sourced from the same flock, of similar parity, identically managed and milked at the same stage of lactation. Also, unlike cows and goats, sheep do not experience a post-partum surge in MSC numbers; counts are generally stable throughout lactation.

Figure 1C:
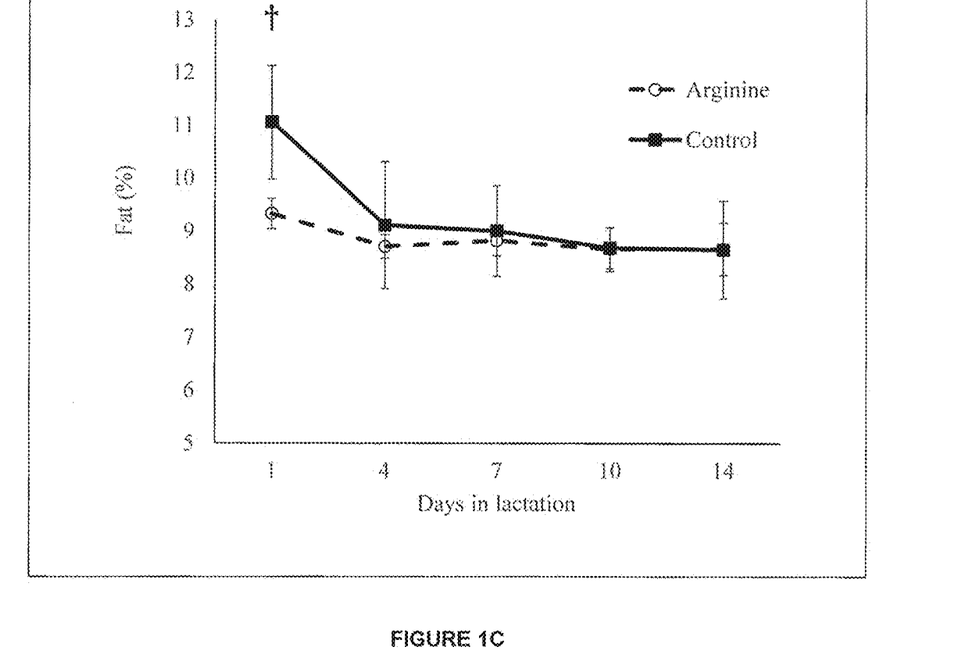
FIG. 1C is a graph from the above study illustrating differences in fat content of milk in L-arginine treated ewes compared to saline-treated control ewes post parturition and L-arginine administration.

There was a trend for increased fat percentage at day 1 in saline-treated controls compared to L-arginine treated ewes (FIG. 1C).

Figure 1D:
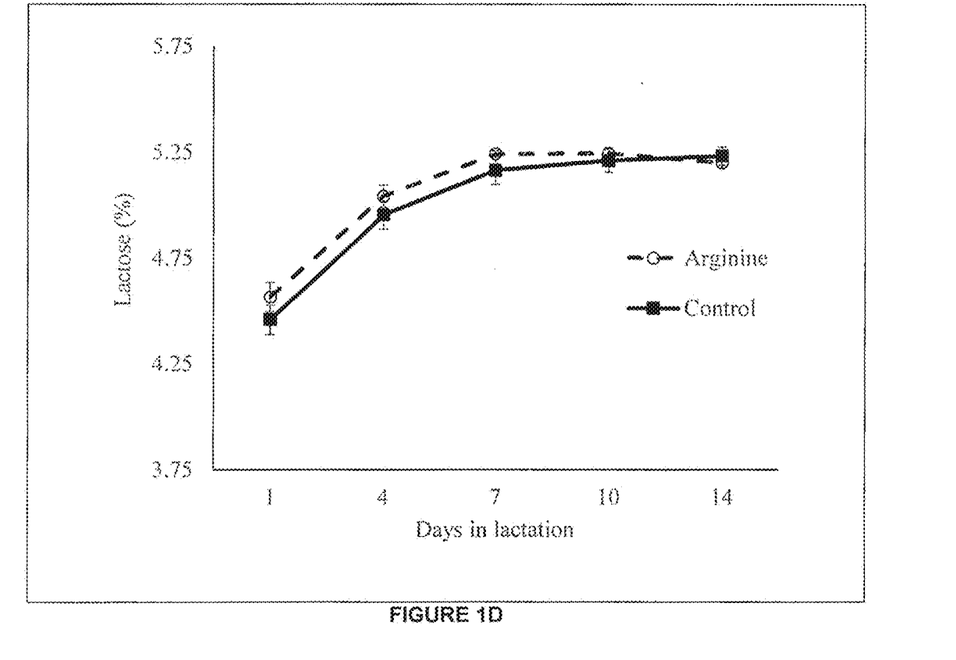
FIG. 1D is a graph from the above study illustrating differences in lactose content of milk in L-arginine treated ewes compared to saline-treated control ewes post parturition and L-arginine administration.
Figure 1E:
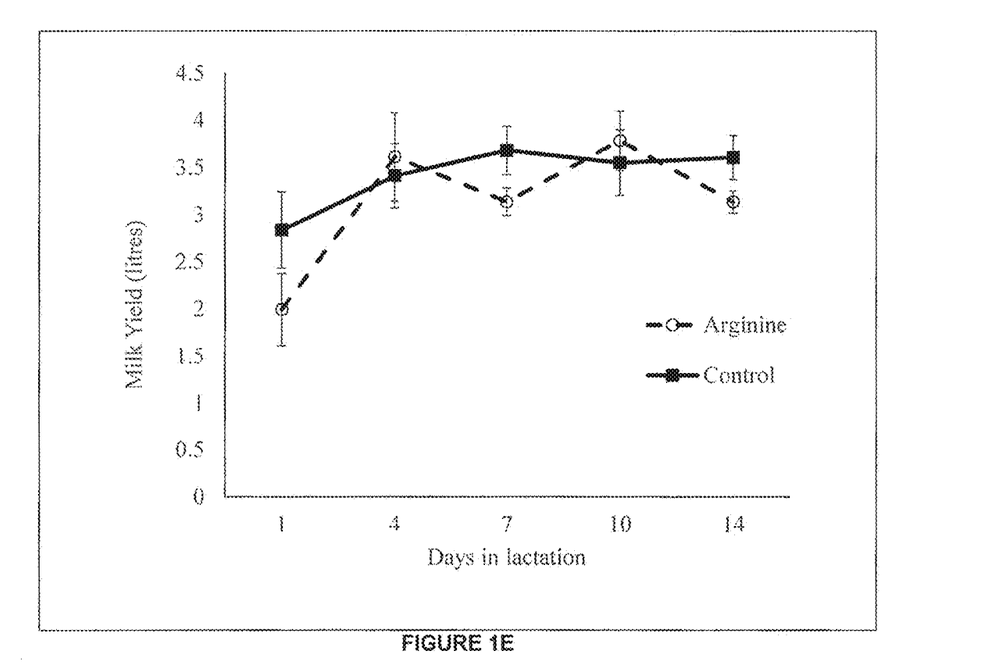
FIG. 1E is a graph from the above study illustrating differences in milk yield in L-arginine treated ewes compared to saline-treated control ewes post parturition and L-arginine administration.

No effect was observed from L-arginine administration on lactose percentage (FIG. 1D), or milk yield (FIG. 1E).

Results—Milk Free Amino Acid Profile

Figure 2A:
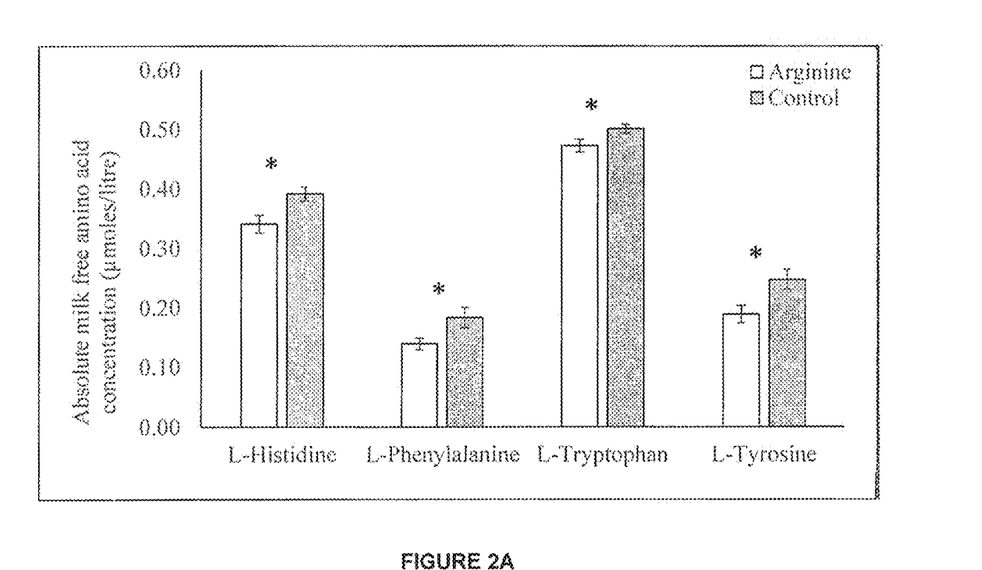
FIG. 2A is a graph from the above study illustrating differences in absolute milk free amino acid concentration at day 7 post parturition in L-arginine treated ewes compared to saline-treated control ewes post parturition and L-arginine administration.

At day 7, absolute concentrations of the L-amino acids histidine, phenylalanine, tryptophan and tyrosine were significantly decreased in saline-treated controls compared L-arginine treated ewes (FIG. 2A).

Figure 2B:
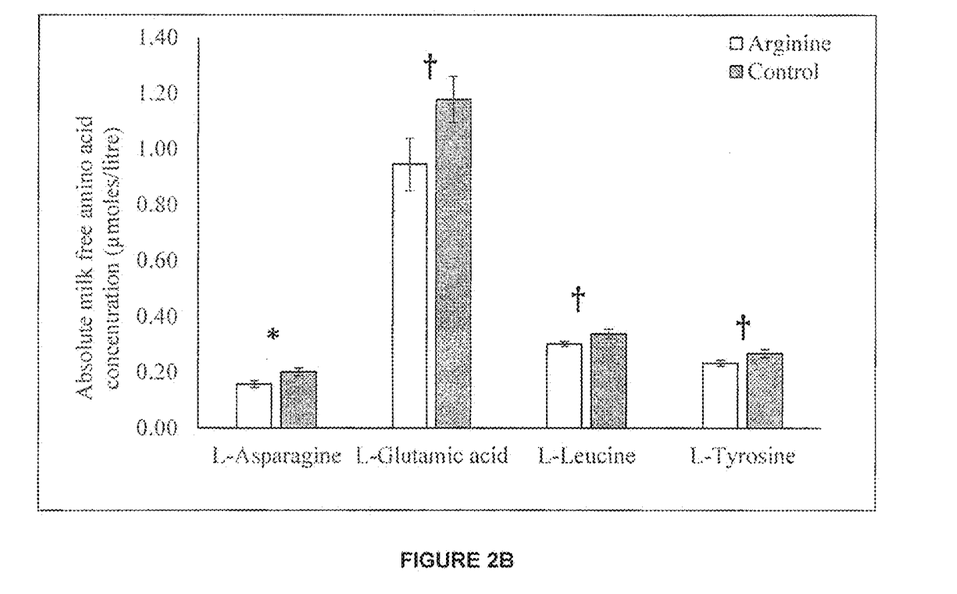
FIG. 2B is a graph from the above study illustrating differences in absolute milk free amino acid concentration at day 14 post parturition in L-arginine treated ewes compared to saline-treated control ewes post parturition and L-arginine administration.

At day 14 (FIG. 2B) asparagine was significantly decreased whilst trends for decreased glutamate, leucine and tyrosine were also observed in saline-treated controls compared to L-arginine treated ewes (FIG. 2B).

Methodology—Effect on Plasma Arginine

To determine the magnitude of the increase in circulating Arg concentrations following a single bolus (3 boluses were given each day), plasma samples collected from all ewes at day 120 of gestation at time −5 (immediately prior to bolus), 30, 60 and 180 minutes following the bolus (Arg or saline) were analysed for Arg concentration using reverse-phase high-performance liquid chromatography (Sales et al., 2012). Nine ewes per treatment group were randomly selected for analysis.

Results—Effect on Plasma Arginine

Figure 4:
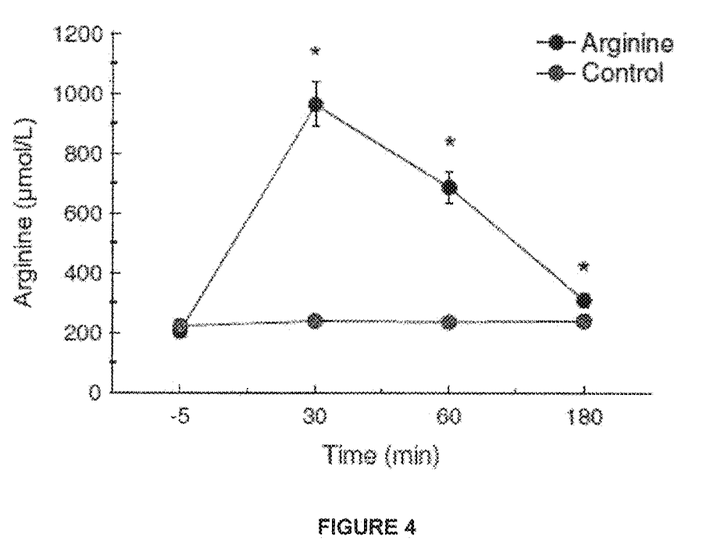
FIG. 4 is a graph from the above study illustrating plasma arginine concentrations immediately prior to (−5 min) and 30, 60 and 180 minutes following an i.v. bolus of arginine or saline (controls) in twin-bearing ewes (n=9/group) at 120 days gestation. Figure shows least square means±standard error.

As illustrated in FIG. 4, a single bolus of Arg resulted in a 4 fold increase in circulating Arg concentrations 30 minutes following i.v. bolus with elevated concentrations (3 times the control) being maintained until at least 60 minutes post-dosage. The lack of difference between the treatment groups immediately prior to the bolus indicates that the circulating concentrations of Arg return to baseline within 3 hours.

Figure 5:
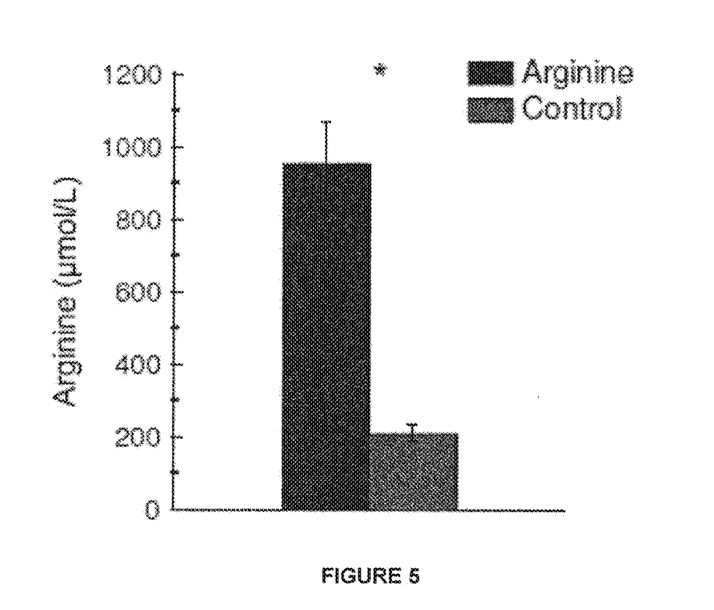
FIG. 5 is a graph from the above study illustrating plasma arginine concentrations 1 hour following a bolus of arginine or saline (controls) and immediately prior to slaughter at day 140 gestation in twin-bearing ewes (n=6/group). Figure shows least square means±standard error.

Plasma profiles were also obtained for a sample ewes slaughtered at 140 days of gestation. The plasma profiles of Arg 1 hour following a bolus and immediately prior to slaughter was 4.6 times higher than controls (P<0.0001). These results are illustrated in FIG. 5. The results confirm the effect of the treatment regime on the circulating concentrations of Arg.

SUMMARY

L-arginine administration from day 100 to parturition decreased milk somatic cell count in twin bearing Romney ewes, maintaining milk composition, and demonstrating the beneficial effect that L-arginine has on mammary gland health and function. The results show that the positive effects attributed to L-arginine administration and the consequent elevated levels of plasma arginine, in terms of milk somatic cell count, provide a protective response for at least 14 days post administration and as a consequence, maintain normal milk yield and composition. These findings may have important implications for the meat and dairy industries where high milk somatic cell counts impact negatively on neonatal growth and the quality of products produced from milk.

Aspects of the methods and uses have been described by way of example only and it should be appreciated that modifications and additions may be made thereto without departing from the scope of the claims herein.

Example 2

In a second experiment ewes were supplemented with arginine during mid-late gestation that stopped at parturition.

Figure 3:
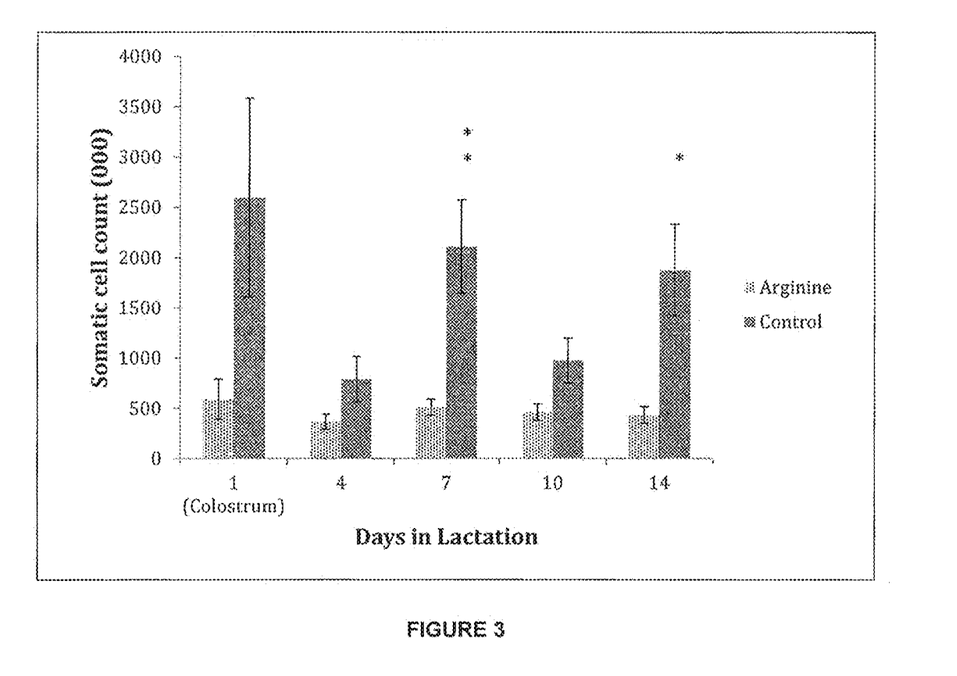
FIG. 3 is a graph from a further study confirming the effect of arginine supplementation from 100 days gestation to birth in twin-bearing ewes on somatic cell count (SCC) in milk. Data was log transformed for analysis—back transformed values are presented. Figure shows least square means with their 95% confidence intervals. **, $P<0.01$; *, $P<0.05$.

A decreased the somatic cell count (SCC) on day 7 and 14 of lactation was measured (~75% lower relative to controls), with similar trends (P<0.15) at day 1 (77% lower than controls) (colostrum) and day 10 (53% lower than controls) of lactation compared to controls (FIG. 3).

In addition the variation in SCC between animals was also greater in the control compared to the arginine-supplemented ewes both at each time-point and over time (FIG. 3).

Ewe age, breed, time of milking (morning vs. afternoon) and stage of lactation can affect milk SCC, however all these factors were identical between treatment and control ewes in this study indicating that the observed differences are due to the treatment effect.

Arginine-supplemented ewes SCC in milk remained at approximately 366,000-589,000 cells/ml throughout the period of study whereas SCC in milk of control ewes ranged from 787,000-2,594,000 cells/ml.

Overall these results indicate that ewes supplemented with arginine have healthier udders compared to the udders in the control ewes.

What is claimed is:

1. A method of decreasing somatic cell count in the milk from a lactating ruminant comprising administering a therapeutically effective amount of L-arginine, NCG or NAG to elevate blood plasma arginine levels in the ruminant, said L-arginine, NCG or NAG administered during the gestation time period and/or during the lactation phase post parturition.

2. A method of improving mammary gland health in a ruminant as measured via somatic cell count in milk produced comprising administering a therapeutically effective amount of L-arginine, NCG or NAG to elevate blood plasma arginine levels, said L-arginine, NCG or NAG administered during the gestation time period and/or during the lactation phase post parturition.

3. The method of claim 1, wherein the ruminant is a bovine, caprine, cervine or ovine species.

4. The method of claim 1, wherein the somatic cell count is at least 10% lower than an equivalent ruminant not receiving L-arginine.

5. The method of claim 1, wherein the somatic cell count in milk from the treated animal is less than approximately 600,000 cells/ml.

6. The method of claim 1, wherein the somatic cell count in milk from the treated animals comprises greater than 90% inactive macrophages.

7. The method of claim 1, wherein the ruminant receives a dose of L-arginine, NCG or NAG, equivalent to at least approximately 100 to 5000 μmol/kg body weight per day.

8. The method of claim 1, wherein the L-arginine, NCG or NAG, is administered orally or parenterally.

9. The method as claimed in claim 8 wherein the L-arginine, NCG or NAG, is formulated prior to administration in a rumen protected form.

10. The method of claim 1, wherein the time period for administration may commence from day 50 to 120 of gestation.

11. The method of claim 1, wherein administration of L-arginine, NCG or NAG, ends at parturition.

12. The method of claim 1, wherein administration of L-arginine, NCG or NAG commences at parturition.

13. The method of claim 1, wherein administration of L-arginine, NCG or NAG, commences during gestation and continues post parturition for at least 1 day.

14. The method of claim 1, wherein somatic cell count remains reduced in milk produced by the lactating ruminant animal for at least 1 day post administration ending.

15. The method of claim 1, wherein somatic cell count remains reduced for at least 14 days post administration ending.

* * * * *